(12) United States Patent
Desrosiers

(10) Patent No.: US 12,252,686 B2
(45) Date of Patent: Mar. 18, 2025

(54) SPIRULINA CULTIVATION PROCESS

(71) Applicant: Myriam Desrosiers, Maliotenam (CA)

(72) Inventor: Myriam Desrosiers, Maliotenam (CA)

(73) Assignee: Myriam Desrosiers, Maliotenam (CA)

( * ) Notice: Subject to any disclaimer, the term of this patent is extended or adjusted under 35 U.S.C. 154(b) by 977 days.

(21) Appl. No.: 17/230,017

(22) Filed: Apr. 14, 2021

(65) Prior Publication Data

US 2021/0348116 A1 Nov. 11, 2021

(30) Foreign Application Priority Data

May 7, 2020 (CA) ...................................... 3080381

(51) Int. Cl.
*C12N 1/12* (2006.01)
*C12N 1/20* (2006.01)

(52) U.S. Cl.
CPC ................. *C12N 1/12* (2013.01); *C12N 1/20* (2013.01); *C12N 2500/14* (2013.01); *C12N 2500/24* (2013.01)

(58) Field of Classification Search
CPC ........................................................ C12N 1/12
See application file for complete search history.

*Primary Examiner* — Ruth A Davis
(74) *Attorney, Agent, or Firm* — BENOIT & COTE

(57) ABSTRACT

The invention relates to a method of cultivating spirulina (*Arthrospira platensis*) in a temperate or northern climate, comprising a period of reproduction of the spirulina strain and a period of dormancy of the spirulina strain when the night temperature of the cultivation tank falls below the limit of 17° C., preferably below the limit of 18° C. or 19° C. or even 20° C., in which, in order to put said spirulina strain into dormancy, a sample volume of the reproduction medium of said strain is taken and placed in conditions of reduced luminosity compared to a sunlight of normal intensity generally borne by said strain during the reproduction period during periods of light alternating with periods of darkness, the said sampling volume is maintained at a temperature of between 5 and 20° C., preferably between 10 and 18° C., under reduced agitation compared with agitation during the reproduction period, at a pH of at least 9, preferably at least 9.5 or at least 10 feeding the sample volume every 4 to 7 days with 5-15%, preferably 10%, of the sample volume of a composition comprising about 1 g/L sea salt, 6 g/L sodium bicarbonate, 2.5 g/L potassium nitrate, 1 g/L potassium sulfate and/or magnesium sulfate, and about 3 g/L sodium and/or calcium carbonate.

11 Claims, No Drawings

SPIRULINA CULTIVATION PROCESS

CROSS-REFERENCE TO RELATED APPLICATIONS

This application claims priority under 35 USC § 119(e) of U.S. provisional patent application 3,080,381 filed on 2020 May 7, the specification of which is hereby incorporated by reference.

BACKGROUND

(a) Field

The present invention relates to a process for growing and cultivating spirulina (*Arthrospira platensis*) suitable for temperate or northern climate.

(b) Related Prior Art

The term "spirulina" can refer to various species of filamentous cyanobacteria. Spirulina" is used herein to refer to the species *Arthrospira platensis*. It is a blue-green bacterium found in organic and soda lakes in the intertropical belt. This bacterium multiplies rapidly and is a food source for some animals as well as for humans. It is industrially cultivated in Africa, India, Peru, Vietnam, China, and more recently in the south of France. Nowadays, it is considered as an interesting food supplement because of its nutritional value. Indeed, it represents a source of proteins (60-70% by weight) and vitamins (about 4% by weight), but is also rich in essential amino acids, minerals, essential fatty acids and antioxidants. It is recognized as having beneficial effects on health, such as antioxidant, immunomodulatory, anti-inflammatory, anti-cancer, anti-viral and anti-bacterial effects, but also positive effects against hyperlipidemia, malnutrition, obesity, diabetes and anemia. Many studies on the effects of spirulina are still in progress.

Spirulina is cultivated in tanks a few centimeters deep, exposed to sunlight, at a temperature generally between 30 and 35° C., in alkaline water with a pH of about 10. The bacteria are filtered, drained, washed and dried to produce a green powder.

In view of the interesting properties of spirulina, and in order to reduce its transportation from the intertropical belt to the northern areas, we try to cultivate it in geographical areas which are originally much less suitable for it, especially because of the reduced light exposure and lower ambient temperatures than those which generally prevail in its natural environment.

SUMMARY

According to an embodiment, there is provided a method for cultivating spirulina (*Arthrospira platensis*) in a temperate or northern climate, comprising a period of reproduction of the spirulina strain and a period of dormancy of the spirulina strain when the night temperature of the cultivation tank falls below the limit of 17° C. in which, in order to put said spirulina strain into dormancy, a sample volume of the reproduction medium of said strain is taken and placed in conditions of reduced luminosity with respect to a sunlight of normal intensity generally borne by said strain during the reproduction period during periods of light alternating with periods of darkness, the said sampling volume is maintained at a temperature of between 5 and 20° C. under reduced agitation compared with agitation during the reproduction period at a pH of at least 9 by supplying the sample volume every 4 to 7 days with 5-15% of the sample volume of a composition comprising about 1 g/L sea salt, 6 g/L sodium bicarbonate, 2.5 g/L potassium nitrate, 1 g/L potassium sulfate and/or magnesium sulfate, and about 3 g/L sodium and/or calcium carbonate.

The light periods may be in register with the daytime durations of the dormancy period, and the dark periods are in register with the nighttime durations of the dormancy period.

The temperature of the medium in the dormant period may vary with the duration of the light period, with the temperature being lower during shorter light periods.

During the dormancy period the medium may be agitated by blowing air at regular intervals.

During the dormancy period, fertilizer may be introduced into the medium in the form of urea, approximately once a month, at a dose of 0.01 g/L to 1 g/L of sample volume.

Iron may be introduced into the medium once a month at a dose of 0.02 to 2 g/L of sample volume and in the form of iron chelate such as EDTA-FeNa·3H2O.

The purging of the culture medium may be performed consisting of a separation of the spirulina and the sludge.

The spirulina strain may be reactivated after a period of dormancy by progressively increasing the luminosity, the temperature of the medium, the concentration of salts and urea as well as the frequency of supply of urea up to a frequency of once a day during the reproduction period.

Features and advantages of the subject matter hereof will become more apparent in light of the following detailed description of selected embodiments, as illustrated in the accompanying figures. As will be realized, the subject matter disclosed and claimed is capable of modifications in various respects, all without departing from the scope of the claims. Accordingly, the drawings and the description are to be regarded as illustrative in nature, and not as restrictive and the full scope of the subject matter is set forth in the claims.

DETAILED DESCRIPTION

The present invention is more particularly directed to providing a process for growing spirulina (*Arthrospira platensis*) suitable for temperate or northern climate, such as Canada or northern European countries.

According to the invention, the method of cultivating spirulina (*Arthrospira platensis*) in a temperate or northern climate, comprises a period of reproduction of the spirulina strain and a period of dormancy of the spirulina strain when the night temperature of the cultivation tank falls below the limit of 17° C., preferably below the limit of 18° C. or 19° C. or even 20° C., method in which, with a view to putting said spirulina strain into dormancy, a sample volume of the reproduction medium of said strain is taken and placed in conditions of reduced luminosity compared with a sunlight of normal intensity generally borne by said strain during the reproduction period during periods of light alternating with periods of darkness, the said sampling volume is maintained at a temperature of between 5 and 20° C., preferably between 10 and 18° C., under reduced agitation compared with agitation during the reproduction period, at a pH of at least 9, preferably at least 9.5 or at least 10 feeding the sample volume every 4 to 7 days with 5-15%, preferably 10%, of the sample volume of a composition comprising about 1 g/L sea salt, 6 g/L sodium bicarbonate, 2.5 g/L potassium nitrate, 1 g/L potassium sulfate and/or magnesium sulfate, and about 3 g/L sodium and/or calcium carbonate.

During the breeding season, Spirulina can be grown in open ponds or in greenhouses, or temporarily in greenhouses and temporarily in the open. The cultivation conditions are classical and known in themselves. The temperature of the culture medium is maintained at 30 to 35° C., and continuous agitation, e.g. by blowing air, is used to allow the organisms to grow without tearing them. A length (calculated in turns) of about 7 turns is generally considered ideal. A sea salt concentration of about 3 to 10 g/L of culture medium, a nitrate concentration (e.g. potassium nitrate) of 1 to 2.5 g/L of culture medium, and a sulfate concentration of 0.5 to 1.5 g/L of culture medium are maintained in order to keep the pH around pH=10. Urea is supplied approximately daily at a dose in the range of 0.01 g/L to 1 g/L, preferably in the range of 0.5 g/L, of culture volume.

Advantageously, during the dormant period, the periods of light are in register with the daytime durations of the dormant period, and the periods of darkness are in register with the nighttime durations of the dormant period.

During the dormant period, the temperature of the medium advantageously varies with the length of the light period, with the temperature being lower during shorter light periods.

According to an advantageous embodiment of the process of the invention, the medium is agitated by blowing air at regular intervals during the dormant period. The reduced agitation allows the spirulina to find its nutrients and to do its mitosis, at a reduced rate, without fracturing them. We then generally obtain longer filaments than in period of reproduction, namely from 15 to 30 turns in dormancy, compared to 5 to 15 turns in period of reproduction.

During the dormant period, fertilizer is advantageously introduced into the medium in the form of urea, about once a month, at a dose of 0.01 g/L to 1 g/L, preferably about 0.5 g/L, of sample volume.

Preferably, iron is introduced into the sample medium once a month at a dose of 0.02 to 2 g/L sample volume, preferably 0.05 to 1 g/L sample volume, more preferably 0.05 to 0.15 g/L sample volume. Even more preferably, the iron is introduced into the medium in the form of iron chelate, especially in the form of $EDTA\text{-}FeNa \cdot 3H_2O$.

Of course, a purge of the culture medium can be performed, consisting of a separation of the spirulina from the sludge, thus promoting the survival of the spirulina during the dormant period, under favorable conditions.

Once the dormancy period is over, we try to reactivate the spirulina strain by progressively increasing the luminosity, the temperature of the medium, by adapting the concentration of salts and urea as well as the frequency of urea feeding up to a frequency of once a day during the reproduction period. It has been found that Spirulina can be easily transferred to culture conditions in this way.

It has been determined that the process of the invention allows the cultivation of spirulina in temperate or even northern climate geographical areas, with acceptable yields, without having to replace the strain at each reproduction cycle. Dormancy is easy and requires little labor and inputs compared to the reproduction period.

The invention is described in more details below in support of an example implementation in Canada.

In this example, Spirulina is grown in greenhouses, which allows for better control of the environment, i.e. temperature, sunlight and inputs to the ponds, and ensures better hygienic control of the ponds. The ponds vary in size from 22.5 to 45 m2, and the greenhouse also contains an 8 m2 spirulina nursery. The level of culture medium in the tank is advantageously maintained constant during the addition of culture medium thanks to the variability of the surface.

Advantageously, the basins include an insulating layer, for example in expanded polystyrene or other, insulating it from the ground. It is also possible to equip the ponds with a heating system, in particular of the underfloor heating type, in order to compensate for the cool nights at the beginning and end of the season. Preferably, an open-work cover is also provided to shade the pools in case of too much light intensity.

The culture medium consists of a solution of mineral salts in water. The culture medium must provide the spirulina with all the chemical elements it needs. The pH of the culture medium must be between 8.0 and 11. There are different recipes of culture medium for spirulina. The example concerns one of the most "comfortable" for Spirulina; it best guarantees ease of cultivation.

The water used must be potable. It should be tested at the beginning of each season for its composition and for bacteria and/or pathogens, but also for heavy metals.

The culture medium contains sea salt, bicarbonate, potassium nitrate, potassium sulfate, magnesium, monoammonium sulfate, and urea. Calcium carbonate is also added for dormancy. The salts and fertilizers are advantageously diluted in water in order to be incorporated into the culture medium.

Another essential parameter of Spirulina culture is the temperature of the culture medium. This directly influences the growth rate of spirulina: although fairly resistant to cold (up to 3-5° C. above zero), spirulina only starts to grow appreciably above 20° C. The growth speed is maximum around 35-37° C. Above this temperature, there is a rapid risk of destruction of the culture, which is certain to occur after a few hours above 43-44° C. It is known that sudden variations of temperature are harmful.

The light is another essential factor. A very strong light (full sun) can be dangerous in the following cases
  on a cold crop (less than 14-15° C.), especially in case of sudden illumination
  on a very hot culture, because it brings an additional heating
  on a very diluted crop (Secchi of more than 6 cm)
  on a crop in difficulty (following an incident for example)
On the other hand, a culture in good conditions of concentration and temperature can be exposed with profit to a maximum of natural light. We voluntarily reduce the luminosity by shading if we wish to slow down the growth of spirulina, or if we are in one of the preceding cases.

Let us note again the agitation as an essential factor in the spirulina culture. It is important to agitate a Spirulina culture in order to promote a homogeneous dispersion of the Spirulina in the culture medium, and its exposure to light. A too violent agitation damages the spirulina by generating fragments and causes the appearance of foam. Advantageously, the agitation is carried out in a continuous way by a small submersible electric pump. For the nursery of smaller volume of culture (less than 100 liters), a continuous agitation by injection of air can be realized by means of a small compressor for aquarium for example. This last method is very practical for the conservation of a backup culture.

When the weather returns in spring, the spirulina is brought out of dormancy and the nursery in the greenhouse is filled. We start with 100 liters of concentrated spirulina. The first days, we increase the volume of the nursery by 10%. The following days, we increase by 20% of the volume that the nursery contains, and then by 30%, taking into account the evaporation of water, but without adding more than 10% of the volume of water per day. The temperature is gradually increased by 1° C. over 5 days until it reaches 22 degrees during the day. The agitation is changed to a continuous agitation. We switch to the breeding feed. Once the nursery is filled (1000 liters) we transfer in the basins with variable geometry. The volume of the tank is increased as it fills up. After one week we can proceed to the first harvest.

The concentration of a culture is evaluated by the intensity of its color. A "Secchi disk" is used for this purpose. This is a graduated ruler with a small white disk attached to the end (perpendicularly). This instrument is immersed in the culture until the disc is no longer visible. The depth of the disk is then read on the graduated ruler. A culture is diluted if the Secchi disk remains visible beyond a depth of 5-6 cm; a value of 2-3 cm corresponds to a culture ready for production. Values below 2 cm indicate the need to dilute the crop, or to harvest heavily. In good conditions, the quantity of spirulina present in a culture doubles every 2 to 4 days, until reaching a maximum concentration (Secchi<1.5 cm). Between 1.5 cm and 3.5 cm, the Secchi scale is roughly linear, with 1.5 cm corresponding to 0.5 g/l (weight of dry spirulina per liter of medium) and 3 cm corresponding to 0.25 g/l.

The pH of the liquid tends to increase as the spirulina grows. From about 8.5 at the beginning (new medium), the pH can increase to 10 or even 11. This last value indicates the need to renew (or dilute) the culture medium.

As mentioned above, when the concentration of the culture goes below a Secchi of 2-3 cm, (about one week after filling the variable geometry tank) we proceed to harvest, preferably in the morning, especially if we want to dry the spirulina.

The water of the basin is advantageously filtered by means of a first passage on a filter followed by a second filtration. A stainless steel filter with a mesh size between 30 and 60 microns is ideal for the second filtration. The liquid that flows out of it should be almost colorless. When the liquid is drained, scrape off the biomass and place it in a sieve covered with a satin percal cloth. After use, the filter should be washed thoroughly, as quickly as possible, and then dried in the shade. The spirulina is then placed on the screen of the press, well wrapped in the cloth. The spirulina is pressed until there is no more liquid, while avoiding that the cells burst and that the spirulina takes a blackish tint.

Once pressed, the spirulina paste contains about 25% by weight of dry matter. Its weight can then be reduced by ¾ by drying. Drying should be conducted as quickly as possible, preferably within 6 hours. If a heated dryer is used, it is advisable to avoid exceeding 60° C. in order not to destroy the vitamins and essential fatty acids contained in the harvested spirulina. To facilitate its drying, the spirulina paste can be extruded in the form of filaments (like spaghetti), placed on a grid and then dried by ventilation away from sunlight. Drying is a good technique to preserve spirulina in the long term.

Fresh spirulina paste should be fairly dark green, almost odorless and tasteless. A reddish-blue tint indicates that it has been pressed too hard, or that it has been stored for too long (in the latter case, it has a rotten egg smell). A good quality dry spirulina should be fairly dark green, with a characteristic odor (algae/mushroom) that is not very pronounced and a weak taste. A turquoise tint indicates a strong exposure to light (safe, but nutritional quality strongly diminished).

In order to avoid a slow deterioration of the culture medium, as well as to compensate for the carbon absorbed by the spirulina, a desired fraction of the culture liquid is regularly renewed. At regular intervals, especially after several months, the tanks should be cleaned by removing the sludge from the bottom. The lost medium must of course be replaced by new medium.

The process of the invention is characterized in particular by a step of putting the spirulina in dormancy before the outside temperature drops to such a point that there is a risk of freezing the ponds. A sampling volume of the culture medium is then taken and filled into an ad hoc tank equipped with interrupted agitation (a few hours during the day and a few hours at night) and placed in conditions of reduced luminosity compared to normal sunlight intensity generally tolerated by said strain during the reproduction period, maintaining said sample volume at a temperature of about 13-14° C., at a pH of about 10, by supplying the sample volume about every 7 days with 10% of the sample volume of a composition comprising about 1 g/L of sea salt, 6 g/L of sodium bicarbonate, 2.5 g/L of potassium nitrate, 1 g/L of potassium sulfate and/or magnesium sulfate, and about 3 g/L of sodium and/or calcium carbonate.

It has been found advantageous to lower the temperature of the culture medium gradually, by about 1° C. over 5 days.

Lighting can be generated by Coolwhite neon lights. The lighting follows the hours of the day. For example, until December 21, the number of hours of lighting is decreased and after December 21, it is increased to follow the sunset and sunrise.

Dormant Spirulina is fed once a week with the above dormancy formula until it is warm enough to re-cultivate in the greenhouse tanks. Urea and iron are added daily during the production period and once a month during the dormant period.

After the dormant period, the crop is gradually returned to the breeding period.

While preferred embodiments have been described above and illustrated in the accompanying drawings, it will be evident to those skilled in the art that modifications may be made without departing from this disclosure. Such modifications are considered as possible variants comprised in the scope of the disclosure.

The invention claimed is:

1. A method for cultivating spirulina strain in a state of dormancy, comprising
   taking a sample volume of a spirulina strain from a reproduction medium of said spirulina strain when the temperature of the reproduction medium falls below 17° C. at night;
   placing said sample volume in a culture medium comprising conditions of reduced luminosity compared with conditions of luminosity during a reproduction period of the spirulina strain comprising alternating periods of light and periods of darkness;
   maintaining the said sample volume at a temperature of between 5° C. and 20° C. and under reduced agitation compared with agitation during the reproduction period of the spirulina strain, at a pH of at least 9 by supplying said sample volume in a culture medium every 4 to 7 days with a volume of a composition corresponding to 5% to 15% of said sample volume in a culture medium, said composition comprising about 1 g/L of sea salt, 6 g/L of sodium bicarbonate, 2.5 g/L of potassium nitrate, 1 g/L of potassium sulfate or magnesium sulfate, and about 3 g/L of sodium or calcium carbonate,
   thereby cultivating the spirulina strain in a state of dormancy and wherein the spirulina strain is cultivated for a period of dormancy.

2. The method of cultivating spirulina strain in a state of dormancy according to claim 1, wherein the alternating periods of light and periods of darkness are in register with daytime durations of the period of dormancy, and nighttime durations of the period of dormancy, respectively.

3. The method of cultivating spirulina strain in a state of dormancy according to claim 1, further comprising varying the temperature of the culture medium during the period of dormancy, the temperature of the culture medium being lower during shorter periods of light.

4. The method of cultivating spirulina strain in a state of dormancy according to claim 1, wherein during the period of dormancy, the culture medium is agitated by blowing air at regular intervals.

5. The method of cultivating spirulina strain in a state of dormancy according to claim 1, wherein, during the period of dormancy, fertilizer is introduced into the culture medium in the form of urea, approximately once a month, at a dose of 0.01 g/L to 1 g/L of sample volume.

6. The method of cultivating spirulina strain in a state of dormancy according to claim 5, further comprising
reactivating the spirulina strain after the period of dormancy by progressively increasing luminosity, the temperature of the culture medium, the concentration of salts and urea as well as the frequency of supply of urea up to a frequency of once a day.

7. The method of cultivating spirulina strain in a state of dormancy according to claim 1, wherein iron is introduced into the culture medium once a month at a dose of 0.02 to 2 g/L of sample volume.

8. The method of cultivating spirulina strain in a state of dormancy according to claim 7 wherein the iron introduced into the culture medium is in the form of iron chelate.

9. The method of cultivating spirulina strain in a state of dormancy of claim 7 wherein the iron chelate is in the form of EDTA-FeNa·3H2O.

10. The method of cultivating spirulina strain in a state of dormancy according to claim 1, wherein a purging of the culture medium is performed consisting of a separation of the spirulina and the sludge.

11. The method of cultivating spirulina strain in a state of dormancy according to claim 1, further comprising
reactivating the spirulina strain after the period of dormancy by progressively increasing luminosity, the temperature of the culture medium, and the concentration of salts.

* * * * *